United States Patent
Kiyohara et al.

(10) Patent No.: US 7,459,699 B2
(45) Date of Patent: Dec. 2, 2008

(54) METHOD OF DETERMINING PROCESSING POSITION IN CHARGED PARTICLE BEAM APPARATUS, AND INFRARED MICROSCOPE USED IN THE METHOD

(75) Inventors: Masahiro Kiyohara, Chiba (JP); Makoto Sato, Chiba (JP); Tatsuya Asahata, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 267 days.

(21) Appl. No.: 11/286,684

(22) Filed: Nov. 23, 2005

(65) Prior Publication Data

US 2006/0118733 A1   Jun. 8, 2006

(30) Foreign Application Priority Data

Nov. 26, 2004   (JP)   ............................. 2004-341729

(51) Int. Cl.
*G01J 1/00* (2006.01)
*G01N 21/00* (2006.01)
*G01N 23/00* (2006.01)

(52) U.S. Cl. ............ 250/491.1; 250/492.2; 250/492.21; 250/307; 250/310; 250/338; 250/338.1; 250/339.11; 250/339.08; 250/341.8; 250/343; 250/346; 430/313; 430/315; 438/401; 438/462; 438/692; 438/16; 438/694; 356/363

(58) Field of Classification Search ............. 250/491.1, 250/492.2, 492.21, 307, 310, 338, 1, 339.11, 250/339.08, 341.8, 342, 343, 346; 430/313, 430/315; 438/401, 462, 692, 16, 694; 356/363

See application file for complete search history.

(56) References Cited

U.S. PATENT DOCUMENTS 5,843,831 A * 12/1998 Chung et al. ................. 438/401
5,985,764 A * 11/1999 Lin et al. ..................... 438/692
6,639,226 B2 * 10/2003 Morio et al. ............. 250/491.1

FOREIGN PATENT DOCUMENTS

| JP | H11-144670 | 5/1999 |
| JP | H11-329315 | 11/1999 |

* cited by examiner

*Primary Examiner*—Jack I Berman
*Assistant Examiner*—Meenakshi S Sahu
(74) *Attorney, Agent, or Firm*—Brinks Hofer Gilson & Lione

(57) ABSTRACT

A laser mark which will be the positioning mark for a secondary charged particle image in the charged particle beam apparatus is applied by moving the sample processing/observation area in the charged particle beam apparatus so as to come into the view field while performing an observation by an infrared microscope, and by a using a laser optical system disposed coaxially with an optical observation system, the mark made at the periphery of the processing/observation object area. Next, by a superposition of an infrared transmission image and a CAD data, the processing/observation object area and the laser mark are registered onto the CAD data. And, by a correlation of the registered data read from the charged particle beam apparatus and the secondary charged particle image, it is possible to accurately and easily determine the processing position.

6 Claims, 2 Drawing Sheets

SECONDARY CHARGED PARTICLE IMAGE

REGISTERED DATA

FIG. 1A　　　　FIG. 1B
INFRARED TRANSMISSION IMAGE　　INFRARED TRANSMISSION IMAGE
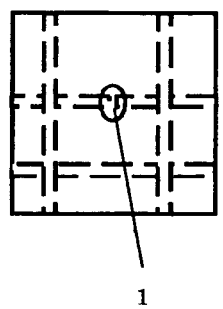 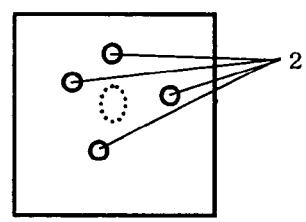
FIG. 1C　　　　FIG. 1D
REGISTERED DATA
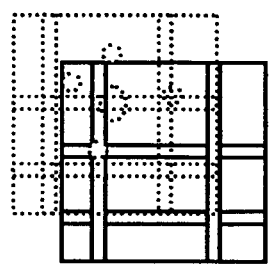 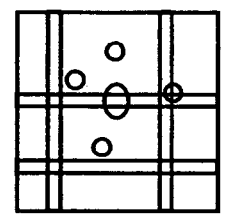
FIG. 1E　　　　FIG. 1F
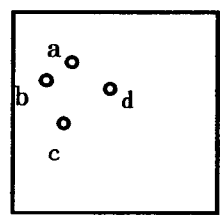 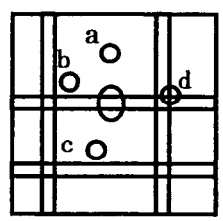 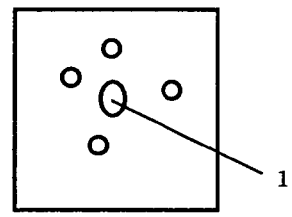
SECONDARY CHARGED PARTICLE IMAGE　　REGISTERED DATA　　SECONDARY CHARGED PARTICLE IMAGE 19 : STORAGE MEANS
18 : ARITHMETIC AND CONTROL MEANS
17 : MEANS FOR REGISTERING LASER MARK TO CAD DATA

METHOD OF DETERMINING PROCESSING POSITION IN CHARGED PARTICLE BEAM APPARATUS, AND INFRARED MICROSCOPE USED IN THE METHOD

This application claims priority under 35 U.S.C. §119 to Japanese Patent Application No. 2004-341729 filed Nov. 26, 2004, the entire content of which is hereby incorporated by reference.

BACKGROUND

The present invention relates to a method determining the processing position of a charged particle beam apparatus such as focused ion beam apparatus (FIB) and scanning electron microscope, and relates especially to a method of determining a processing position below the sample surface, which cannot be seen by a visible light optical microscope, and a laser microscope used in the method.

In a processing positioning in a conventional charged particle beam apparatus, the processing position has been determined by a superposition of a visible light optical microscope image and a secondary charged particle image by a charged particle beam irradiation (for example, refer to Patent Document 1). Or, the processing position has been determined by performing a marking by a laser optical system disposed coaxially with a visible light optical observation system in the vicinity of a processing/observation object area, and by a superimposition of the optical image in a place where the marking has been performed and the secondary charged particle image (for example, refer to Patent Document 2).

[Patent Document 1] JP-A-11-144670 (4th-5th pages, FIGS. 3-4)

[Patent Document 2] JP-A-11-329315 (4th page, FIG. 1)

In the conventional processing positioning, in a case where the processing/observation area exists below the sample surface and an upper layer is not a transparent film like an insulating film, there has been the problem that the processing area cannot be observed by a visible light optical microscope. Further, there have been the problems that, even in the case where the surface is a transparent film like the insulating film and the processing/observation object area can be observed by the visible light optical microscope, it is impossible to perform a laser marking because there exists no absorption of the laser beam in the insulating film and, in a case where no characteristic shape exists on the sample surface, the superposition cannot be performed by the secondary charged particle image and the visible light optical microscope image, by which only the sample surface can be observed.

It is the goal of the present invention to solve the above issues and thereby provide an application to provide, in a sample comprising a wiring pattern of a semiconductor sample such as an IC, a technique for a sample whose wiring pattern layer is covered by an opaque film, which does not depend on the sample surface shape, thereby accurately and easily performing the processing positioning in the charged particle beam apparatus.

BRIEF SUMMARY

In order to solve the above problem, in the present invention, there are provisions so that, by performing an observation by an infrared microscope and performing the laser marking on the periphery of the processing/observation area, it is possible to identify this area in the secondary charged particle image even in the case where no characteristic shape exists in the sample surface, and additionally the processing positioning is performed by registering the processing/observation object area and a laser marking place onto CAD data after a superposition of a transmission image by infrared observation and the CAD data, reading the registered data on a charged beam device, and correlating the secondary charged particle image and the registered data.

Further, in a case of the sample in which there exists no absorption of the laser as in the case of the insulating film for instance, it is possible to perform the processing positioning by forming ahead of time a deposition film on the sample surface by the charged particle beam, observing the processing/observation area by the infrared microscope, and performing the laser marking onto the deposition film.

An optical observation system capable of the infrared observation and a laser optical system for marking disposed coaxially with the former may be a device composite with the charged beam device, or separate devices.

The present invention brings about such advantages as described below.

By using the infrared microscope for the optical observation system, in addition to a transparent sample, it is possible to observe a wiring layer while transmitting through for instance an Si substrate used in a device.

Further, by performing the laser marking, it is possible to observe by the secondary charged particle image irrespective of the sample surface in the charged particle beam apparatus.

Further, even in the case of the sample in which there exists no absorption of the laser as in the case of the insulating film, it is possible to observe by the secondary charged particle image by forming ahead of time the deposition film on the periphery of the processing/observation object area, and performing the laser marking onto the deposition film.

Additionally, by the superposition of the transmission image made by the observation of the secondary charged particle image and the CAD data, it is possible to highly accurately perform the processing positioning by the charged particle beam apparatus by registering the processing/observation object area and the laser mark onto the CAD data, and correlating the registered data read from the charged particle beam apparatus and the secondary charged particle image.

Further, by using the CAD data, not only the correction of the display magnification rate of the secondary charged particle image to coincide with the optical microscope image, but also it is possible to arbitrarily change the display magnification of the CAD data so as to coincide with the secondary charged particle image, and so it is possible to facilitate the processing positioning by the charged particle beam apparatus.

BRIEF DESCRIPTION OF THE DRAWINGS

FIGS. 1A-1F are diagrams showing process examples of positioning for processing in a charged particle beam apparatus utilizing an infrared microscope and CAD data.

DETAILED DESCRIPTION OF THE PREFERRED EMBODIMENTS

Figure 2:
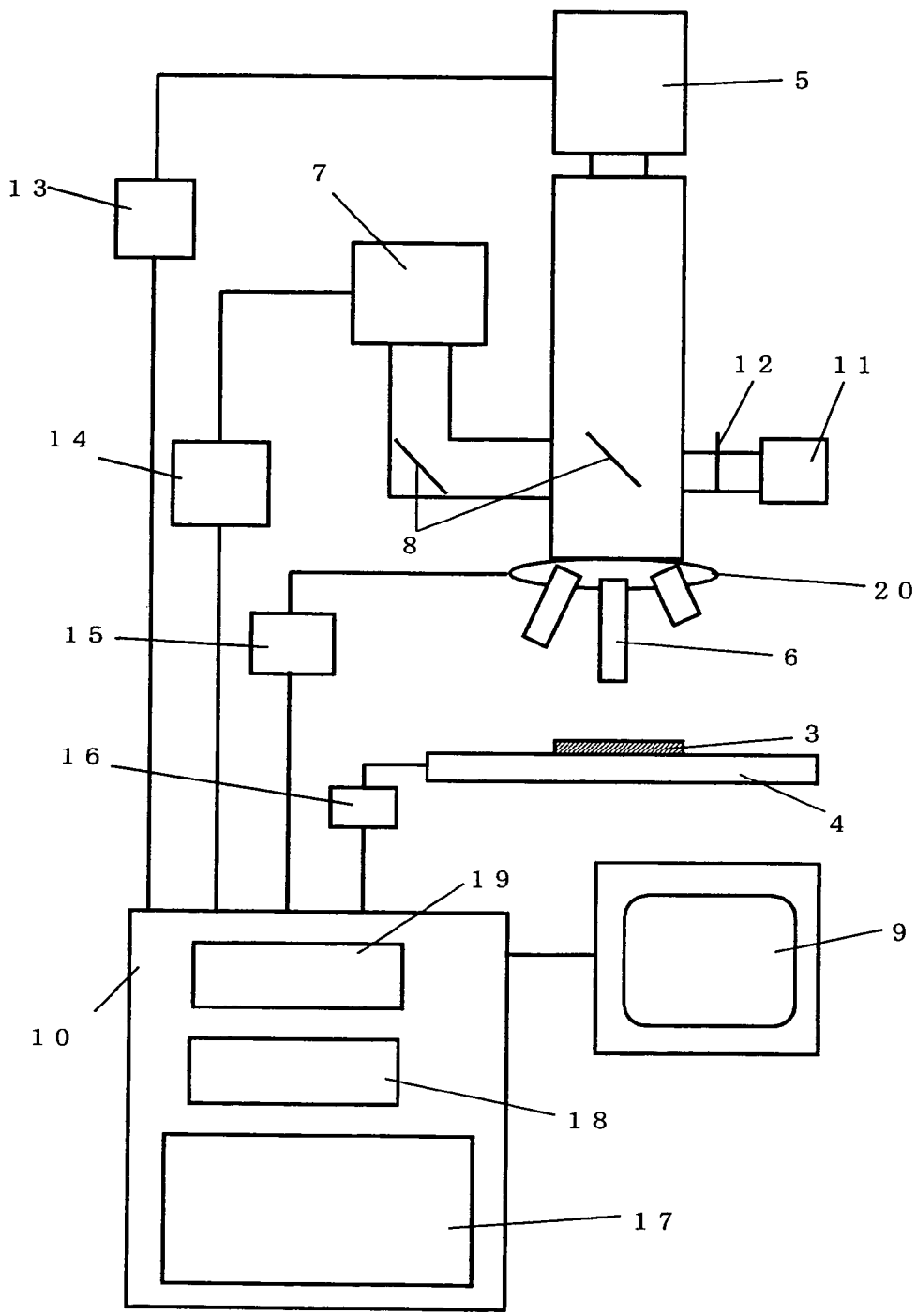
FIG. 2 is a schematic diagram showing one example of an infrared microscope with laser function.

An embodiment of the present invention will here be explained by referring to the drawings. FIG. 1 is one showing figures of a sample in various steps of the processing positioning in the charged particle beam apparatus utilizing the infrared microscope and the CAD data. The steps comprise:

(A) 1st step: finding the processing/observation area 1 by an observation by the infrared microscope from the back face of the sample (FIG. 1A), (B) 2nd step: for the setting mark of the secondary charged particle image in the charged particle beam apparatus, performing a laser marking 2 at the periphery of the processing/ observation object area by the laser optical system disposed coaxially with the infrared microscope (FIG. 1B), (C) 3rd step: superimposing the CAD data and the infrared transmission image at the periphery of the processing/observation area by using a software for CAD data processing and by an alignment between a transmission image (broken line portion) by the observation of the infrared microscope and the CAD data (solid line portion) (FIG. 1C), (D) 4th step: registering the processing/observation area and the laser mark onto the CAD data (FIG. 1D), (E) 5th step: performing a position correction by a movement of a sample stage or a beam shift in the charged particle beam apparatus and a correction, such as alteration of the display magnification, of a charged particle beam irradiation optical system by correlating respective arbitrary laser marks a, b, c, and d in order on the secondary charged particle image of the charged particle beam apparatus and on the above registered data, which have been simultaneously displayed on each of plural monitors or one monitor, thereby matching the registered data with the secondary charged particle image (FIG. 1E), and (F) 6th step: a process of performing the processing positioning by displaying, after performing the above correlation, the processing/observation object area 1 on the secondary charged particle image (FIG. 1F).

FIG. 2 is a schematic diagram of one example of an infrared microscope with laser function. A sample 3 is set onto a movable stage 4. An infrared CCD camera 5 obtains the infrared transmission image of the sample 3. By causing, from the light generated from the sample illumination 11, only the light whose wavelength is that desired to be transmitted by a wavelength selection filter 12, an infrared observation and also a visible observation become possible. The movable stage 4 operates also in a Z direction besides X, Y and in-plane rotation directions, and can infer the film thickness from the difference between the Z coordinate when obtaining the infrared transmission image and the Z coordinate when there is visible observation of the sample surface. By this, it becomes the reference depth information for the processing in the charged particle beam apparatus, and the end point detection becomes easy. Incidentally, this operation in the Z direction may be controlled by an operation of the infrared microscope lens-barrel. An image can be obtained by an arbitrary objective lens 6 with an arbitrary magnification. A laser generated from a laser optical system 7 is aimed at the sample 3 by beam splitters 8 so as to become coaxial with the optical axis of the infrared correspondence CCD camera 5. Next, CAD data stored in a storage means 19 of a computer 10 is displayed onto a monitor 9. An alignment of the CAD data displayed onto the monitor 9 and the infrared transmission image is performed. The infrared transmission image and the CAD data are superimposed by moving the movable stage 4 to align the periphery of the processing/observation area. And, for the mark of the secondary charged particle image in the charged particle beam apparatus, the marking is performed at the periphery of the processing/observation area by the laser 7, and the processing/observation area and the laser mark are registered onto the CAD data. This registration is performed by means 17 for registering the laser mark on the CAD, within the computer 10. Incidentally, this laser marking may be performed in a point in time at which the infrared transmission image has been obtained. All operations can be performed by the computer 10 while observing the processing/observation area through the monitor 9. Control units 13, 14, 15 and 16 input a control signal from an arithmetic and control means 18 of the computer 10, and control respectively the CCD camera 5, the laser optical system 7, a revolver 20 and the movable stage 4. The registered data is read in the charged particle beam apparatus by a PC for controlling the charged particle beam apparatus, and the processing position is determined by correlating the secondary charged particle image and the registered data which has been read.

The invention claimed is:

1. A method for determining the processing position in a charged particle beam apparatus, comprising:
    disposing a semiconductor sample having a wiring pattern below a sample surface of the semiconductor sample, on a sample stage;
    moving the sample stage in order to get a processing/observation area on the wiring pattern in the charged particle beam apparatus below the sample surface into view field of an infrared microscope while observing a transmission image by the infrared microscope;
    performing a laser marking on the sample surface at a periphery of the processing/observation area before or after superposing an infrared microscope observation image containing the processing/observation area to a CAD data corresponding to the wiring pattern containing the processing/observation area;
    registering the processing/observation area and a position of the laser marking of the infrared microscope observation image onto the CAD data;
    observing a secondary charged particle image of the position of the laser marking in the charged particle beam apparatus; and
    positioning the processing/observation area by correlating the secondary charged particle image to the position of the laser marking on the CAD data that has been registered during the registering the processing/observation area.

2. The method of claim 1, wherein the performing a laser marking is performed by a laser that is aimed at the sample so as to be coaxial with an optical axis of the infrared microscope.

3. The method of claim 1, wherein prior to the disposing a semiconductor sample a deposition film is formed on the semiconductor sample so as to enable the performing a laser marking.

4. The infrared microscope of claim 1, further comprising a sample illumination that causes light to be directed towards the sample and results in formation of the infrared transmission image.

5. An infrared microscope with laser marking function, comprising:
    a three-dimensionally movable stage for disposing a sample;
    a CCD camera for obtaining an infrared transmission image of the sample;
    a laser optical system for applying a laser mark to a periphery of a processing/observation area obtained from the infrared transmission image;
    a storage means for storing CAD data of the sample;
    a monitor for displaying the CAD data stored in the storage means and the infrared transmission image; and
    means for registering the processing/observation area and the laser mark on the CAD data after superposing the CAD data and the infrared transmission image on the monitor by moving the three-dimensionally movable stage.

6. The infrared microscope of claim 5, wherein the laser optical system is disposed coaxially with an optical axis of the CCD camera.

* * * * *